United States Patent [19]

Treace

[11] 4,014,337
[45] Mar. 29, 1977

[54] EVACUATOR DEVICE

[75] Inventor: Harry T. Treace, Forest Hill, Tenn.

[73] Assignee: Richards Manufacturing Company, Inc., Memphis, Tenn.

[22] Filed: Mar. 26, 1976

[21] Appl. No.: 671,005

[52] U.S. Cl. ............................................. 128/278
[51] Int. Cl.² ......................................... A61M 1/00
[58] Field of Search .......................... 128/276–278, 128/350, 226, 230, 231, 232, 145.7, 297–300, 349, 285; 32/33

[56] References Cited
UNITED STATES PATENTS

| | | | |
|---|---|---|---|
| 3,115,138 | 12/1963 | McEluenny et al. | 128/278 |
| 3,324,855 | 6/1967 | Heimlich | 32/33 |
| 3,376,868 | 4/1968 | Mondiadis | 128/278 |
| 3,572,340 | 3/1971 | Lloyd et al. | 128/278 |
| 3,763,857 | 10/1973 | Schrading | 128/276 |
| 3,856,013 | 12/1974 | Dulle | 128/285 |
| 3,871,377 | 3/1975 | Treace | 128/278 |

Primary Examiner—Robert W. Michell
Assistant Examiner—Henry S. Layton
Attorney, Agent, or Firm—John R. Walker, III

[57] ABSTRACT

A device for use in evacuating waste fluid from a closed wound or the like in a patient's body. The evacuation device includes an expansible member enclosed within a substantially collapsible pouch having walls formed of an air- and liquid-impermeable material. At least one hollow tube is attached to the pouch in operative communication with the interior of the pouch so that when the end of the hollow tube opposite the pouch is positioned within a closed wound or the like and when the expansible member is compressed and subsequently released, suction is applied to the wound through the hollow tube as the expansible member and the pouch expand thereby drawing any waste fluid in the wound into the interior of the pouch. The expansible member may consist of a hydrophylic sponge so that when waste fluid is drawn into the interior of the pouch, the expansible member will swell as a result of the contact between it and the waste fluid. A compression sleeve may be provided for holding the expansible member and the pouch in a compressed condition until it is desired to use the evacuation device to evacuate waste fluid from a closed wound. A conveyor member is provided within the interior of the pouch for conveying waste fluid through the evacuation device and is particularly useful when the evacuation device is used in conjunction with a central vacuum unit.

11 Claims, 6 Drawing Figures

U.S. Patent   Mar. 29, 1977   4,014,337
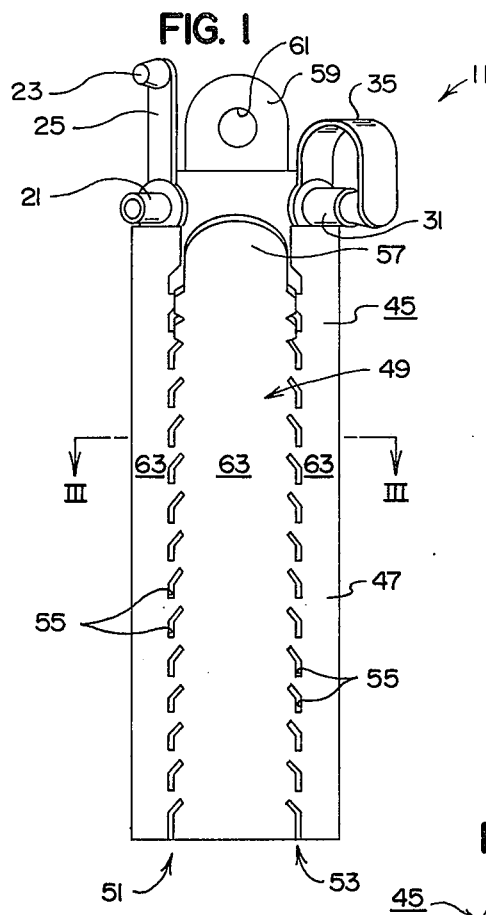
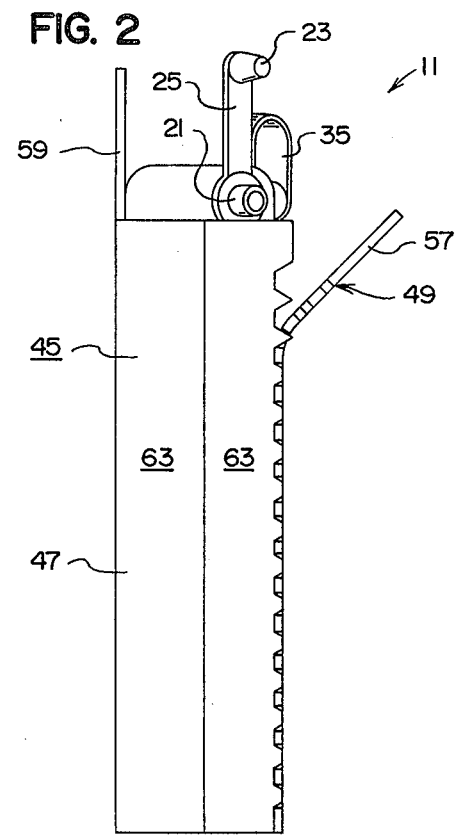
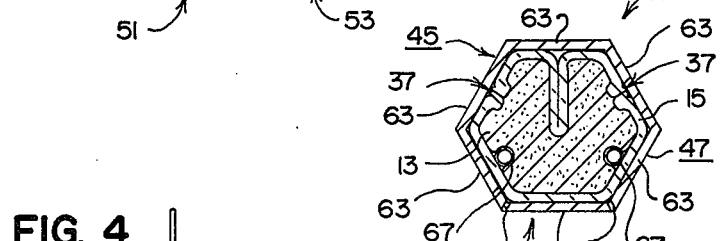
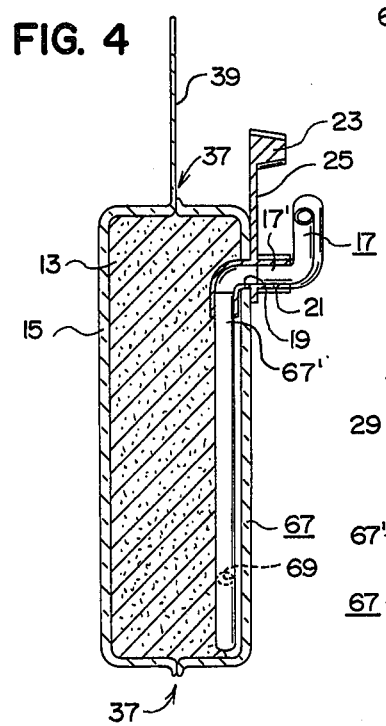
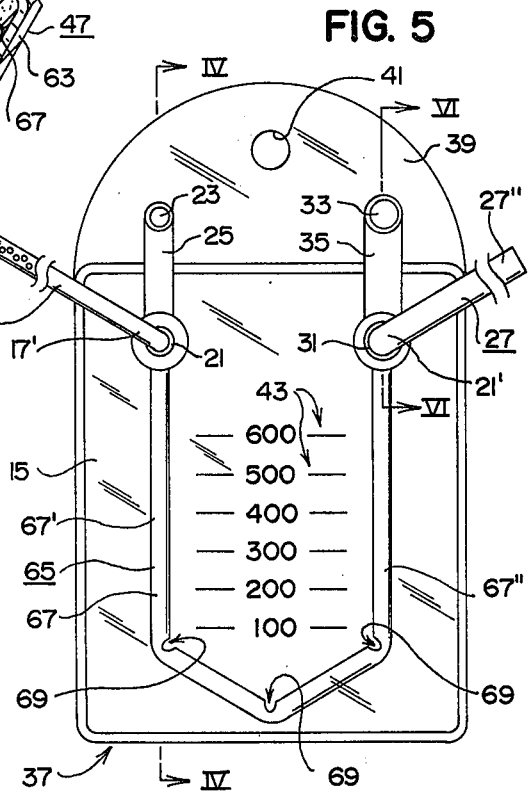

4,014,337

EVACUATOR DEVICE

BACKGROUND OF THE INVENTION

1. Field of the Invention

This invention relates generally to means for evacuating waste fluid from closed wounds or the like and more specifically to portable means for applying continuous suction to such a closed wound and to thereby draw waste fluid therefrom.

2. Description of the Prior Art

Various means have been developed for applying continuous suction to a closed wound to thereby draw waste fluid therefrom. Perhaps the most common method of applying continuous suction to a closed wound is by positioning one end of a hollow tube within the closed wound and attaching the other end of the hollow tube to an outlet of a central vacuum system as is typically provided on the walls of hospital rooms or to a portable electrical aspirator. This method is satisfactory where the patient is bedridden, but is not satisfactory where the patient is ambulatory. Portable evacuation devices have been developed for use where the patient is ambulatory. See, for example, McElvenny et al., U.S. Pat. Nos. 3,115,138; Mondiadis, 3,376,868; Lloyd et al., 3,572,340; and Treace, 3,871,377. The McElvenny et al patent discloses an evacuation device in which spring members are enclosed within an expandable chamber so that when the chamber is compressed and subsequently released, the spring members will cause it to expand and thereby create a vacuum within the interior of the chamber. The Mondiadis patent discloses an evacuation device in which the walls of an expandable chamber are resilient so that when the chamber is compressed and subsequently released, the walls of the chamber will cause it to expand and thereby create a vacuum within the interior of the chamber. The Lloyd and Treace patents disclose evacuation devices in which resilient foam material is enclosed within a collapsible container so that when the container is compressed and subsequently released, the resilient property of the foam material will cause the container to expand and thereby create a vacuum within the interior of the container. While these devices do provide portable evacuation of closed wounds on ambulatory patients, they do not perform entirely satisfactorily. One problem with such evacuation devices is the unevenness of the strength and duration of the suction applied to the closed wound. One reason for this is because these evacuation devices require the expansible means (i.e., the spring members, the walls of the expandable chamber, and the resilient foam material) to be manually compressed and the strength and duration of the vacuum created by the subsequent expansion of the expansible means is determined by how much it was compressed which is, in turn, largely determined by the strength of the person doing the compressing. Thus, with persons of varying strength compressing such a device, the strength and duration of the vacuum created thereby varies. Another problem with such devices occurs when it is desired to use the portable evacuation device in conjunction with a central vacuum unit when a patient is ambulatory only part of the time. Prior portable evacuation devices were adapted to be used in conjunction with a central vacuum unit or the like by allowing a tube to be selectively attached between the interior of the portable evacuation device and the central vacuum unit so that the central vacuum unit could draw waste fluid from the closed wound through the portable evacuation device (e.g., see lines 42–55 of col. 10 of the Lloyd et al patent). However, such a method is disadvantageous in that substantial amounts of the waste fluid is dissipated in the interior of the portable evacuation device as it is drawn therethrough.

SUMMARY OF THE INVENTION

The present invention is directed towards overcoming the problems and disadvantages of prior evacuation devices. One concept of the present invention is to form the expansible means of a portable evacuation device of a hydrophylic foam so that suction will be created not only by the mere expansion of the expansible means due to its elastic recovery but also as a result of the swelling of the hydrophylic foam material as it absorbs any waste fluid drawn therein. Another concept of the present invention is to provide a portable evacuation device with a compression sleeve for holding the expansible means thereof in a compressed condition until it is desired to use the evacuation device to evacuate waste fluid from a closed wound so that the vacuum created by similar evacuation devices will be substantially of the same strength and duration. Another concept of the present invention is to provide the interior of a portable evacuation device with conveyor means for conveying waste fluid through the interior of the evacuation device particularly when the evacuation device is used in conjunction with a central vacuum unit or portable electrical aspirator while preventing any substantial amount of the waste fluid from being dissipated in the interior of the evacuation device as it is drawn therethrough.

BRIEF DESCRIPTION OF THE DRAWINGS

FIG. 1 is a front elevational view of the evacuation device of the present invention.

FIG. 2 is a side elevational view of the evacuation device of the present invention showing the compression sleeve thereof being removed from the expansible means thereof.

FIG. 3 is a cross-sectional view of the evacuation device of the present invention as taken on line III—III of FIG. 1.

FIG. 4 is a cross-sectional view of the expansible means and the substantially collapsible pouch of the evacuation device of the present invention as taken on line IV—IV of FIG. 5.

FIG. 5 is a front elevational view of the expansible means and the substantially collapsible pouch of the evacuation device of the present invention showing first and second hollow tubes attached thereto for connecting the evacuation device to a closed wound and to an outlet of a central vacuum unit.

FIG. 6 is a sectional view of a portion of the present invention as taken on line VI—VI of FIG. 5.

DESCRIPTION OF THE PREFERRED EMBODIMENT

The evacuation device 11 of the present invention is for evacuating waste fluid or the like from a closed wound or the like in a patient's body. The evacuation device 11 is of the type that includes an expansible means 13 enclosed within a substantially collapsible pouch 15.

The substantially collapsible pouch 15 is formed of an air- and liquid-impermeable material such as flexible plastic or the like so as to make the pouch 15 substantially air-tight. A first hollow tube 17 (see FIG. 5) is provided for selectively connecting the evacuation device 11 to a closed wound or the like in a patient's body so that when the expansible means 13 and the pouch 15 are released after having been compressed, suction will be applied to the wound through the first hollow tube 17 to draw any waste fluid in the wound into the interior of the pouch 15. More specifically, the pouch 15 is provided with a first aperture or opening 19 for allowing the first end 17' of the first hollow tube 17 to be selectively attached to the pouch 15 adjacent the first opening 19 in operative communication with the interior of the pouch 15 (see FIG. 4). The evacuation device 11 preferably includes a first tubular connector member 21 fixedly attached to the pouch 15 adjacent and surrounding the first opening 19 therein. The first tubular connector member 21 is adapted to frictionally engage the first end 17' of the first hollow tube 17 so as to operatively connect the first hollow tube 17 to the pouch 15 in operative communication with the interior of the pouch 15. The first end 17' of the first hollow tube 17 may include a removable adapted portion (not shown) for allowing different sizes of hollow tubes to be attached to the pouch 15 through the first tubular connector member 21. A stopper 23 may be provided for selectively closing the first tubular connector member 21 for reasons which will hereinafter become apparent. A flexible strap 25 is preferably provided for connecting the stopper 23 to the first tubular connector member 21 to prevent the stopper 23 from being misplaced or the like.

A second hollow tube 27 (see FIG. 5) may be provided for selectively connecting the evacuation device 11 to an outlet (not shown) of a central vacuum system such as is typically provided on the walls of most hospital rooms or to a portable electrical aspirator so that the evacuation device 11 can be used in conjunction with such a central vacuum unit or portable electrical aspirator. More specifically, the pouch 15 is provided with a second opening 29 for allowing the first end 27' of the second hollow tube 27 to be selectively attached to the pouch adjacent and surrounding the second opening 29 in operative communication with the interior of the pouch 15 (see FIG. 6). Preferably, the evacuation device 11 includes a second tubular connector member 31 fixedly attached to the pouch 15 adjacent to and surrounding the second opening 29. A stopper 33 may be provided for selectively closing the second tubular connector member 31 for reasons which will hereinafter become apparent. A flexible strap 35 may be provided for connecting the stopper 33 to the second tuular connector member 31 to prevent the stopper 33 from becoming misplaced or the like.

It should be noted that the pouch 15 may be made of two sheets of air- and liquid-impermeable, flexible plastic integrally joined to one another as at the seal 37 to form the pouch 15. A tab 39 or the like may be provided on the pouch 15 for allowing the pouch 15 to be easily attached to a patient in a manner to be hereinafter explained. An aperture 41 is preferably provided through the tab 39 for aiding in the attachment of the pouch 15 to the body of a patient. The air- and liquid-impermeable, flexible plastic that the pouch 15 may be made of is preferably transparent or translucent for allowing the amount of waste fluid drawn into the pouch 15 during use of the evacuation device 11 to be viewed. Indicia 43 may be provided on the pouch 15 for allowing the quantity of waste fluid present in the pouch 15 to be easily and quickly determined.

The expansible means 13 is preferably formed of a hydrophylic sponge material of a type well known to those skilled in the sponge material art having substantially high elastic recovery properties, having substantial fluid absorbency and fluid retaining capacity, and having the characteristic of expanding or swelling when it is contacted by a fluid. The sponge material is preferably of a size that substantially fills the interior of the pouch 15 when fully expanded.

The evacuation device 11 preferably includes a compression sleeve means 45 for selectively holding the expansible means 13 and the pouch 15 in a compressed condition until it is desired to use the evacuation device 11 to draw waste fluid from a closed wound (see FIGS. 1, 2 and 3). The compression sleeve means 45 includes a hollow body member 47 for surrounding the expansible means 13 and the pouch 15 to hold the expansible means 13 and the pouch 15 in a compressed condition. The hollow body member 47 preferably includes tear strip means 49 for allowing the hollow body member 47 to be easily and quickly removed from around the expansible means 13 and the pouch 15 when it is desired to use the evacuation device 11 to evacuate waste fluid from a closed wound or the like. The tear strip means 49 is preferably defined by a pair of perforated seams 51, 53 (see FIG. 1). Each of the perforated seams 51, 53 is composed of a plurality of spaced apart perforations 55 formed in the hollow body member 47 by any means well known to those skilled in the art. The tear strip means 49 preferably includes a tab 57 for allowing the tear strip means 49 to be easily gripped when it is desired to remove the hollow body member 47 from around the expansible means 13 and pouch 15. A second tab 59 may be provided on the hollow body member 47 for allowing the evacuator device 11 to be attached to a suitable place, as the bed or to the body of a patient, or the like. The hollow body member 47 is preferably constructed of a cardboard material or the like which allows easy tearing of the perforated seams 51, 53 when it is desired to remove the hollow body member 47 from the expansible means 13 and the pouch 15. The hollow body member 47 preferably includes at least five substantially rectangular panel members 63 (six being shown in the drawings) with each longitudinal edge of each of the panel members 63 being attached to the longitudinal edge of another of the panel members 63 so as to cause the hollow body member 47 to have a polygonal cross-sectional shape as shown in FIG. 3. The perforated seams 51, 53 are preferably provided substantially adjacent each longitudinal edge of one of the panel members 63 for allowing that panel member 63 to be easily and quickly torn from the adjacent panel members 63 to thereby allow the hollow body member 47 to be easily and quickly removed from around the expansible means 13 and the pouch 15. It should be noted that the polygonal cross-sectional shape of the hollow body member 47 allows the hollow body member 47 to be easily gripped when it is desired to remove the tear strip means 49 therefrom. That is, when it is desired to remove the tear strip means 49 from the hollow body member 47, the hollow body member 47 is held in one hand with the thumb and fingers of that hand gripping the two panel members 63 that are attached to the longitudinal edges of the panel member 63 that is to be removed, and the tab 57 of the tear strip means 49 is gripped with the other hand and pulled away from the hollow body member 47. This provides a secure grip since the two panel members 63 that are gripped to hold the hollow body member 47 are located at an angle relative to the panel member 63 that is to be removed that is less than 180° because of the polygonal cross-sectional shape of the hollow body member 47.

The evacuation device 11 preferably includes conveyor means 67 positioned within the pouch 15 for conveying waste fluid from the first opening 19 in the pouch 15 to the second opening 29 in the pouch 15. The conveyor means 65 includes a hollow tube 67 having a first end 67' attached to the pouch 15 adjacent to and in operative communication with the first opening 19 through the pouch 15 (see FIG. 4) and includes a second end 67" attached to the pouch 15 adjacent to and in operative communication with the second opening 29 through the pouch means 15 (see FIG. 6). The tube 67 includes at least one aperture 69 (three being shown in FIG. 5) intermediate the first and second ends 67', 67" thereof for allowing waste fluid to pass therethrough when the evacuation device 11 is being used to draw waste fluid from a wound. The apertures 69 are preferably located substantially adjacent the bottom of the pouch 15 so as to cause any waste fluid being drawn into the pouch 15 to pass from the tube 67 substantially adjacent the bottom of the pouch 15 so as to allow the amount of waste fluid drawn therein to be accurately and readily ascertained according to the indicia 43. It should be noted that when the evacuation device 11 is used in conjunction with a central vacuum system or a portable electrical aspirator, the waste fluid will be drawn through the tube 67 by the vacuum produced by the central vacuum system so that no substantial amount of the waste fluid will dissipate in the interior of the pouch 15 through the aperture 69. The tube 67 is preferably constructed of a substantially non-collapsible plastic material.

The use of the evacuation device 11 is quite simple. The second end 17" of the first hollow tube 17 is normally placed within a wound in a patient's body as the wound is being sutured closed. The first end 17' of the first hollow tube 17 may then be attached to the evacuation device 11 by being inserted into the first tubular connector member 21. To apply suction to the wound to draw waste fluid therefrom, the compression sleeve means 45 is merely removed from the expansible means 13 and the pouch 15 by tearing the tear strip means 49 therefrom after making sure the second tubular connector member 31 is closed by the stopper 33. Suction will then be applied to the wound through the first hollow tube 17 as the resiliency of the expansible means 13 causes the pouch 15 to expand and as the waste fluid causes the expansible means 13 to swell. However, if it is desired to use the evacuation device 11 in conjunction with a source of vacuum such as a central vacuum system or a portable electrical aspirator, the compresion sleeve means 45 may be left around the expansible means 13 and the pouch 15 and the first end 27' of the second hollow tube 27 is attached to the evacuation device 11 by being inserted into the second tubular connector member 31 and the second end 27" of the second hollow tube 27 is attached to a wall outlet of the central vacuum system or to the portable electrical aspirator. Suction will then be applied to the wound through the first hollow tube 17 to draw any waste fluid in the wound through the first hollow tube 17, the conveyor means 65, the second hollow tube 27 and into the portable electrical aspirator or the central vacuum system which normally has a reservoir for receiving such waste fluid. The evacuation device 11 can then be subsequently used to draw waste fluid from the wound when the patient becomes ambulatory or the like by merely disconnecting the second hollow tube 27 from the evacuation device 11, closing the second tubular connector member 31 with the stopper 33, and removing the compression sleeve means 45 from the expansible means 13 and the pouch 15. When it is subsequently desired to remove and/or replace the evacuation device 11, the first hollow tube 17 is removed from the evacuation device 11, the first tubular connector member 21 is closed with the stopper 23 to prevent escape of any waste fluid from the interior of the pouch 15, and the evacuation device 11 is disposed of. Another evacuation device 11 may then be connected to the first hollow tube 17 to continue the evacuation of the wound or the first hollow tube 17 may then be removed from the wound in a manner well known to those skilled in the art. The hollow tube 17 may be provided with a clamp or the like (not shown) for selectively preventing any waste fluid from escaping therethrough while an evacuation device 11 is being attached thereto.

Athough the invention has been described and illustrated with respect to a preferred embodiment thereof, it is not to be so limited since changes and modifications may be made therein which are within the full intended scope of the invention.

I claim:

1. A closed wound evacuation device for drawing waste fluid from a closed wound in a patient's body, said evacuation device comprising:
   a. a substantially collapsible pouch formed of an air- and liquid-impermeable material having a first opening therethrough for allowing a first end of a first hollow tube to be selectively attached thereto adjacent said first opening therethrough and in operative communication with the interior of said pouch; and
   b. expansible means enclosed within said pouch so that when the first end of the first hollow tube is attached to said pouch and when the second end of the first hollow tube is positioned within a closed wound in a patient's body and when said expansible means is compressed and subsequently released, the expansion of said expansible means will cause suction to be applied to the wound through the second end of the hollow tube to draw any waste fluid in the wound into the interior of said pouch, said expansible means being formed of a hydrophilic sponge material so that when waste fluid is drawn into the interior of said pouch and contacts said expansible means, said expansible means will swell thereby applying further suction to the wound.

2. The closed wound evacuation device of claim 1 in which is included compression sleeve compression sleeve means for holding said expansible means and said pouch in a compressed condition until it is desired to use said closed wound evacuation device to evacuate waste fluid from a closed wound.

3. The closed wound evacuation device of claim 2 in which said pouch has a second opening therethrough for allowing a first end of a second hollow tube to be attached thereto adjacent said second opening and in operative communication with said interior of said pouch so that when the second end of the first hollow tube is positioned within a closed wound in a patient's body and when the second end of the second hollow tube is attached to a source of vacuum, suction is applied to the wound through the second end of the first hollow tube to evacuate waste fluid from the wound; and in which is included conveyor means positioned within said pouch for conveying waste fluid from said first opening in said pouch to said second opening in said pouch, said conveyor means including a hollow tube having a first end attached to said pouch adjacent said first opening therethrough and having a second end attached to said pouch adjacent said second opening therethrough.

4. A closed wound evacuation device for drawing waste fluid from a closed wound of a patient's body; said evacuation device comprising:
 a. a substantially collapsible pouch formed of an air- and liquid-impermeable material having a first opening therethrough for allowing a first end of a first hollow tube to be selectively attached thereto adjacent said first opening and in operative communication with the interior of said pouch;
 b. expansible means enclosed within said pouch so that when the first end of the first hollow tube is attached to said pouch in operative communication with the interior thereof and when the second end of the first hollow tube is positioned within a closed wound in a patient's body and when said expansible means and said pouch are compressed and subsequently released, suction is applied to the wound through the second end of the first hollow tube to draw any waste fluid in the wound into the interior of said pouch; and
 c. compression sleeve means for selectively holding said expansible means and said pouch in a compressed condition until it is desired to use said closed wound evacuation device to draw waste fluid from a closed wound.

5. In a closed wound evacuation device of the type including expansible means enclosed within a substantially collapsible pouch formed of air impermeable material having a first opening therethrough for allowing a first end of a hollow tube to be attached thereto adjacent said first opening therethrough and in operative communication with the interior of said substantially collapsible pouch so that when the first end of the hollow tube is attached to said pouch and when the second end of the hollow tube is positioned within a closed wound in a patient's body and when said expansible means is compressed and subsequently released, suction is applied to the wound through the second end of the hollow tube to draw any waste fluid in the wound into said evacuation device; the combination with said expansible means and said substantially collapsible pouch of compression sleeve means for holding said expansible means and said substantially collapsible pouch in a compressed condition until it is desired to use said closed wound evacuation device to evacuate waste fluid from a closed wound.

6. The combination of claim 5 in which said compression sleeve means includes a hollow body member for surrounding said expansible means and said substantially collapsible pouch to hold said expansible means and said substantially collapsible pouch in a compressed condition.

7. The combination of claim 6 in which said hollow body member of said compression sleeve means includes tear strip means for allowing said hollow body member to be easily and quickly removed from around said expansible means and said substantially collapsible pouch when it is desired to use said closed wound evacuation device to evacuate waste fluid from a closed wound.

8. The combination of claim 6 in which said hollow body member of said compression sleeve means includes at least five substantially rectangular panel members with each longitudinal edge of each of said panel members attached to the longitudinal edge of another of said panel members and in which a plurality of perforations is provided substantially adjacent each longitudinal edge of one of said panel members for allowing said one of said panel members to be easily and quickly torn from the adjacent ones of said panel members to thereby allow said hollow body member to be easily and quickly removed from around said expansible means and said substantially collapsible pouch when it is desired to use said closed wound evacuation device to evacuate waste fluid from a closed wound.

9. The combination of claim 8 in which said hollow body member of said compression sleeve means includes a tab portion attached to said one of said panel members thereof for allowing said one of said panel members to be easily grasped when it is desired to remove said hollow body member from around said expansible means and said substantially collapsible pouch.

10. In a closed wound evacuation device of the type including expansible means enclosed within a substantially collapsible pouch formed of air- and liquid-impermeable material having a first opening therethrough for allowing a first end of a first hollow tube to be attached thereto adjacent said first opening and in operative communication with the interior of said pouch and having a second opening therethrough for allowing a first end of a second hollow tube to be attached thereto adjacent said second opening and in operative communication with the interior or said pouch so that when the second end of the first hollow tube is positioned within a closed wound in a patient's body and when the second end of the second hollow tube is attached to a source of vacuum, suction is applied to the wound through the second end of the first hollow tube to evacuate waste fluid from the wound; the combination with said substantially collapsible pouch of conveyor means positioned within said pouch for conveying waste fluid from said first opening in said pouch to said second opening in said pouch, said conveyor means including a hollow tube having a first end attached to said pouch adjacent said first opening therethrough and having a second end attached to said pouch adjacent said second opening therethrough.

11. The combination of claim 10 in which said hollow tube of said conveyor means includes at least one aperture intermediate said first and second ends thereof for allowing waste fluid to pass therethrough when said closed wound evacuation device is being used to draw waste fluid from the wound.

* * * * *